US010813746B2

(12) United States Patent
Cornelussen et al.

(10) Patent No.: US 10,813,746 B2
(45) Date of Patent: Oct. 27, 2020

(54) PROSTHETIC VALVE FOR REGULATING FLUID FLOW

(71) Applicant: Medtronic, Inc., Minneapolis, MN (US)

(72) Inventors: Richard Cornelussen, Maastricht (NL); Asimina Glynou, Maastricht (NL); Pascalle Reiters, Gronsveld (NL); Robert Vestberg, Charbonniere les Bains (FR); Ulrich Wolfhard, Essen (DE)

(73) Assignee: Medtronic, Inc., Minneaplis, MN (US)

( * ) Notice: Subject to any disclaimer, the term of this patent is extended or adjusted under 35 U.S.C. 154(b) by 0 days.

(21) Appl. No.: 16/317,143

(22) PCT Filed: Jul. 12, 2017

(86) PCT No.: PCT/IB2017/054201
§ 371 (c)(1),
(2) Date: Jan. 11, 2019

(87) PCT Pub. No.: WO2018/011725
PCT Pub. Date: Jan. 18, 2018

(65) Prior Publication Data
US 2019/0254813 A1    Aug. 22, 2019

(30) Foreign Application Priority Data

Jul. 12, 2016   (EP) .................................... 16179067

(51) Int. Cl.
*A61F 2/24*   (2006.01)
(52) U.S. Cl.
CPC .............. *A61F 2/24* (2013.01); *A61F 2/2403* (2013.01); *A61F 2/2409* (2013.01);
(Continued)

(58) Field of Classification Search
CPC ............ A61F 2/24–2424; A61F 2/2475; A61F 2250/0051
See application file for complete search history.

(56) References Cited

U.S. PATENT DOCUMENTS

2007/0208417 A1*  9/2007  Agnew .................. A61F 2/2418
                                                      623/1.24
2016/0008128 A1*  1/2016  Squara .................. A61F 2/2412
                                                      623/2.11

FOREIGN PATENT DOCUMENTS

EP        2606855 A1   6/2013
WO   2017103833 A1   6/2017

OTHER PUBLICATIONS

International Search Report and Written Opinion issued in International Application No. PCT/IB2017/054201 dated Oct. 30, 2017.
(Continued)

*Primary Examiner* — Rebecca S Preston
(74) *Attorney, Agent, or Firm* — Carter, DeLuca & Farrell LLP

(57) ABSTRACT

The invention relates to a prosthetic valve (1) for regulating fluid flow between an upstream side (4) and a downstream side (5) and being operable between an open status and a closed status. The prosthetic valve comprises: —an orifice (2) arranged in a surrounding member (3) and extending between the upstream side (4) and the downstream side (5) wherein in the open status of the prosthetic valve (1) the fluid flow through the orifice is maximally enabled and wherein in the closed status of the prosthetic valve the fluid flow through the orifice in a restriction direction (21) from the downstream side (5) to the upstream side (4) is restricted; and—a leaflet (6) arranged in the orifice and being operable between an open status corresponding to the open status of the prosthetic valve and a closed status corresponding to the closed status of the prosthetic valve. The prosthetic valve (Continued)

further comprises regurgitation means (8, 15, 115, 22) arranged in the prosthetic valve for achieving regurgitation in the restriction direction and arranged for becoming ineffective after a period of deployment.

7 Claims, 6 Drawing Sheets

(52) U.S. Cl.
CPC ..... *A61F 2/2412* (2013.01); *A61F 2210/0004* (2013.01); *A61F 2230/0006* (2013.01); *A61F 2250/003* (2013.01); *A61F 2250/0023* (2013.01); *A61F 2250/0024* (2013.01); *A61F 2250/0031* (2013.01); *A61F 2250/0059* (2013.01); *A61F 2250/0069* (2013.01)

(56) References Cited

OTHER PUBLICATIONS

Extended European Search Report for Application No. 20170467.3 dated Jul. 8, 2020.

\* cited by examiner

PROSTHETIC VALVE FOR REGULATING FLUID FLOW

CROSS-REFERENCE TO RELATED APPLICATIONS

The present application is a U.S. National Stage Application under 35 U.S.C. § 371 of International Application Number PCT/IB2017/054201, filed on Jul. 12, 2017, which claims the benefit of, and priority to, European Application No. 16179067.0 filed Jul. 12, 2016.

The invention relates to a prosthetic valve for regulating fluid flow between an upstream side and a downstream side and being operable between an open status and a closed status; comprising an orifice arranged in a surrounding member and extending between the upstream side and the downstream side wherein in the open status of the prosthetic valve the fluid flow through the orifice is maximally enabled and wherein in the closed status of the prosthetic valve the fluid flow through the orifice in a restriction direction from the downstream side to the upstream side is restricted; and a leaflet arranged in the orifice and being operable between an open status corresponding to the open status of the prosthetic valve and a closed status corresponding to the closed status of the prosthetic valve.

The heart of a human body comprises a number of valves, such as the mitral valve and the aortic valve. The mitral valve of a human patient may dysfunction for instance allowing some degree of blood regurgitation. Due to the blood regurgitation, the left ventricle experiences a higher preload compared with a healthy situation. In addition, the left ventricle experiences a lower afterload compared with a healthy situation. The heart can be seen as a muscle and may have become accustomed to the higher preload and the lower afterload.

Depending on the dysfunction, a prosthetic mitral valve is placed to replace the function of the original mitral valve. However, the left ventricle of the heart may experience a sudden increase in the afterload and a decrease in the preload and when ejecting blood through the aortic valve during systole, the left ventricle may experience a higher blood pressure than that experienced with the diseased mitral valve. This could lead to left ventricle failure with potentially fatal consequences for a patient.

An object of the present invention is to provide a prosthetic valve for replacement of a diseased natural valve having a functionality that changes over a period of time from an initial functionality to a final functionality allowing the patient's body can adapt to the final functionality.

The object is achieved by a prosthetic valve according to the invention, characterized by regurgitation means arranged in the prosthetic valve for achieving regurgitation in the restriction direction and arranged for becoming ineffective after a period of deployment.

Regurgitation in the restriction direction is a functionality of the prosthetic valve. As the regurgitation means becomes ineffective after a period of deployment, the final functionality does not include the regurgitation in the restriction direction. As the regurgitation means becomes ineffective after a period of deployment, the patient's body has the period of deployment to adapt from its status before implanting the prosthetic heart valve, via the regurgitation after the deployment to the status wherein the regurgitation means no longer effectively cause regurgitation.

When the prosthetic valve is in use as a mitral valve, the regurgitation will allow blood to leak back and a higher preload and lower afterload will be obtained.

Preferably the leaflet is displaceable by the fluid flow.

By being displaceable by the fluid flow, the prosthetic valve does not need a source of artificial energy. This is advantageous for surgical applications as there is no source of artificial energy that needs replacement, the prosthetic valve can be small and no connections to a source of artificial energy need to be made.

In a preferred embodiment, the regurgitation means are arranged for gradually becoming ineffective after a period of deployment.

As the regurgitation means become gradually ineffective, the patient's body has the period of deployment to gradually adapt and for instance become train and increase the strength of the relevant heart muscles.

In a preferred embodiment the regurgitation means comprise a member arranged in the orifice on the surrounding member or the leaflet, the member being further arranged to leave a temporary opening in the orifice in the closed state of the prosthetic valve, and wherein the member promotes tissue growth on the member itself, the tissue growth gradually extending the tissue over the temporary opening until the temporary opening is covered.

A temporary opening in the orifice, makes that regurgitation is possible. As the tissue growth gradually extends over the temporary opening, the opening becomes smaller thereby restricting the regurgitation. When in use the temporary opening is covered, the regurgitation through the temporary opening is no longer possible and the regurgitation means have become ineffective.

In a preferred embodiment the member is attached to the surrounding member or the leaflet, leaving the temporary opening between the surrounding member and the leaflet.

A temporary opening between the surrounding member and the leaflet in the closed position, makes that regurgitation is possible. As the tissue growth gradually extends over the temporary opening, the opening becomes smaller thereby restricting the regurgitation. When in use the temporary opening is covered, the regurgitation through the temporary opening is no longer possible and the regurgitation means have become ineffective.

In a preferred embodiment the prosthetic valve comprises a further leaflet arranged in the orifice and being operable between a further open state corresponding to the open status of the prosthetic valve and a further closed state corresponding to the closed state of the prosthetic valve, wherein the member is attached to the leaflet leaving a temporary opening between the leaflet and another leaflet.

In many prosthetic valves, there is more than one leaflet. This embodiment provides an alternative for the embodiment wherein the member is attached to the surrounding member.

In a preferred embodiment the member is a scaffold.

A scaffold has an open structure which means that fluid may flow through it as long as it is not covered by tissue. In addition, scaffolds are advantageous in the stimulation of tissue growth.

In a preferred embodiment, the scaffold is made from a biodegradable material.

In a preferred embodiment the regurgitation means comprise a spring-loaded mechanism embedded in the prosthetic valve achieving a temporary opening for regurgitation, arranged such that the winding or the unwinding of the spring-loaded mechanism achieves the closure of said opening.

In a preferred embodiment the prosthetic valve comprises a further leaflet arranged in the orifice and being operable between a further open state corresponding to the open status of the prosthetic valve and a further closed state corresponding to the closed state of the prosthetic valve, wherein the leaflet is suspended in the orifice from an axle and the further leaflet is suspended in the orifice from a further axle and wherein the winded spring loaded mechanism holds the first axle and the second axle separated from each other and, whereupon unwinding of the spring loaded mechanism, said spring loaded mechanism moves the axle and the further axle towards each other.

By moving the axle and the further axle towards each other, the leaflet and the further leaflet are moved together. That way the temporary opening between the leaflet and the further leaflet that existed at an initial, larger distance can be decreased, which means that the regurgitation decreases.

In a preferred embodiment the spring-loaded mechanism comprises a material degrading over time, whereupon degrading of the material releases and unwinds the spring-loaded mechanism.

The degrading of material is a process that can reliably be engineered to take place at the desired rate.

In a preferred embodiment the spring-loaded mechanism is arranged to gradually unwind.

By gradually unwinding, the temporary opening is gradually closed, which means that the regurgitation means gradually become ineffective and the body in which the prosthetic valve is placed can gradually adapt.

In a preferred embodiment the spring-loaded mechanism comprises a spring arranged in the surrounding member and principally extending in a plane perpendicular to the restriction direction.

As the surrounding member is deformable and as the spring is arranged in the surrounding member and principally extends in the plane perpendicular to the restriction direction, the prosthetic valve has flexibility to deform in the plane perpendicular to the restriction direction.

In a preferred embodiment, the regurgitation means comprise a further orifice arranged in the surrounding member and extending between the upstream side and the downstream side, wherein the regurgitation means are arranged to promote tissue growth in the further orifice when in use to achieve closure of the further orifice after a period of deployment.

By comprising a further orifice, regurgitation is possible even if the leaflet would completely close the orifice. Because the regurgitation means promote tissue growth in the further orifice and tissue grows gradually, regurgitation through the further orifice will gradually become less, i.e. the regurgitation means will gradually become less effective. As the in the end closure of the further orifice is achieved, the regurgitation means become ineffective after a period of deployment.

In a preferred embodiment, the regurgitation means are arranged to promote tissue growth in the further orifice by comprising a scaffold arranged in the further orifice.

Various embodiments of the invention will now be described by way of example only with reference to the figures. Where equal numbers are used in the figures, similar features are referred to.

FIG. 1B is a downstream view (i.e. from the upstream side), FIGS. 1A, 1C and 1D are cross section in the open state, the initial closed state and the final closed state.

FIG. 5A shows a downstream view, FIG. 5B shows a cross section of a spring-loaded mechanism.

Figure 1A:
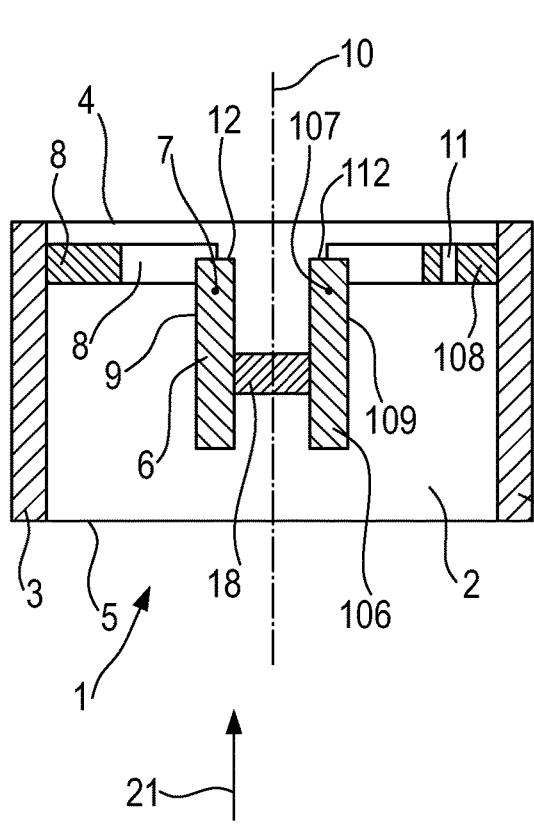
FIGS. 1A, 1B, 1C and 1D show a prosthetic valve according to a first embodiment of the invention.

Herein, degrading can take for instance take the form of decaying or eroding.

In a first embodiment of the invention a prosthetic valve (1) comprises an orifice (2) arranged in a surrounding member (3). This embodiment is depicted in FIGS. 1A, 1B, 1C and 1D. The orifice (2) extends from an upstream side (4) to a downstream side (5). The orifice (2) is cylindrical and comprises a cylindrical axis (10) that intersects the upstream side (4) and the downstream side (5) and an orifice diameter. The prosthetic valve (1) is a mitral valve.

Figure 1B:
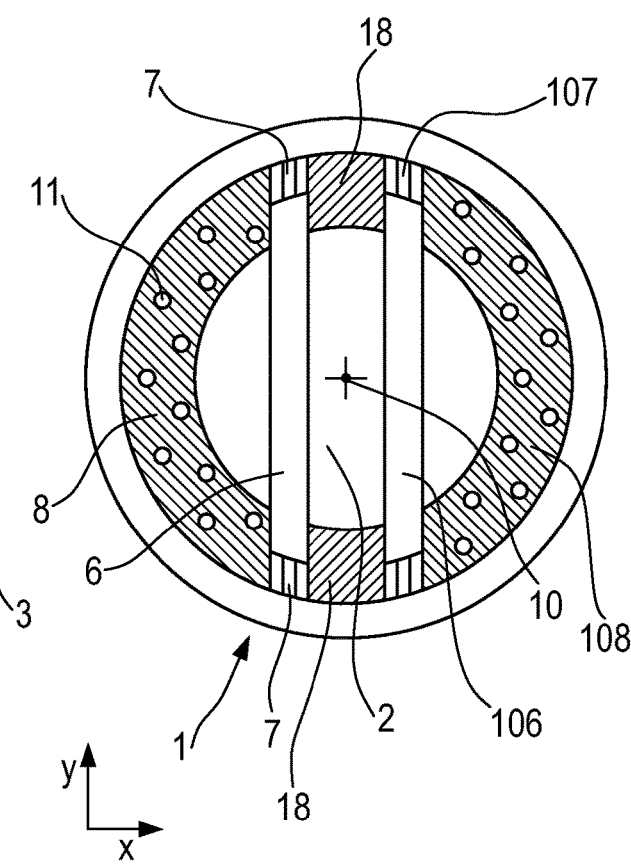

The view in FIG. 1b is a downstream view, i.e. it is a view in the direction from the upstream side (4) to the downstream (5) side.

The cylindrical axis (10) runs in a z-direction of an orthogonal, Cartesian coordinate system.

The prosthetic valve (1) comprises a leaflet (6). The leaflet is suspended in the orifice (2) by an axle (7) around which it can rotate. The prosthetic valve (1) comprises a further leaflet (106) that is suspended in the orifice (2) by a further axle (107) around which it can rotate.

The axle (7) and the further axle (107) run in a y-direction, perpendicular to the z-direction.

The leaflet (6) and the further leaflet (106) are displaceable by being rotable by the blood flow. The leaflet (6) comprises an upstream surface (9) and the further leaflet (106) comprises a further upstream surface (109). The upstream surface (9) of the leaflet (6) and the further upstream surface (109) of the further leaflet (106) each form half a circle, complementing each other to form a full circle. The diameter of the half circle formed by both the leaflet (6) and the further leaflet (106) is smaller than the orifice diameter. The leaflet (6) comprises a coaptating surface (12) and the further leaflet (106) comprises a further coaptating surface (112).

The prosthetic valve (1) has an open status and a closed status. In the open status the leaflet (6) and the further leaflet (106) are in an open position and a further open position respectively.

The open status is depicted in FIG. 1A and FIG. 1B. In the open status, the upstream surface (9) and the further upstream surface (109) face away from each other.

In the open position the cylindrical axis (10) is parallel to the upstream surface (9). In the open position, the coaptating surface (12) and the further coaptating surface (112) face toward the upstream side (4).

Figure 1C:
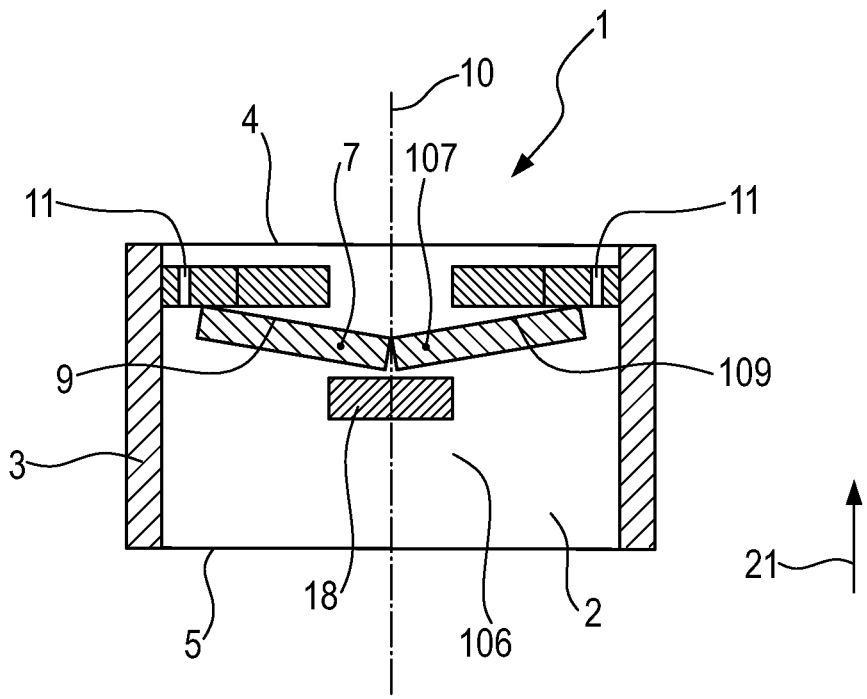

The closed status before deployment, here referred to as initial closed status, is depicted in FIG. 1C. In the closed status the leaflet (6) and the further leaflet (106) cooperate to close the orifice (2).

In the initial closed position the upstream surface (9) is tilted with respect to the plane perpendicular to the cylindrical axis (10) wherein the tilt is such that the angle of rotation from the open position is slightly more than 90 degrees. In this position, the flow of blood through the orifice (2) is restricted in a restriction direction (21) which runs from the downstream side (5) to the upstream side (4). The further upstream surface (109) is also at a titled orientation obtained after slightly more than 90 degrees rotation from the further open position.

The prosthetic valve (1) comprises a ridge (8) and a further ridge (108) arranged in the orifice (2) on the surrounding member (3). The ridge (8) and the further ridge (108) each comprise an edge at an inner diameter that is smaller than the diameter of the half circle. The ridge (8) is arranged at such a position in the orifice (2) that the rotation of the leaflet (6) is stopped by the ridge (8). Similarly, the further ridge (108) is arranged at such a position in the orifice (2) that the rotation of the further leaflet (106) is stopped by the further ridge (108).

The ridge (8) and the further ridge (108) are formed by a scaffold (15) and a further scaffold (115) respectively. Scaffolds are well known in tissue engineering. In this embodiment, the scaffold (15) and the further scaffold (115) are made from a porous polylactide. The scaffold (15) and the further scaffold (115) are hemocompatible.

The scaffold (15) and the further scaffold (115) each comprise one or more temporary openings formed by pores and allows blood to pass through the one or more temporary openings.

Thus, the scaffold (15) is a member that is comprised by regurgitation means. Similarly, the scaffold (115) is a member that is comprised by regurgitation means.

In a variant of the embodiment (not shown), the leaflet (6) and the further leaflet (16) leave an opening between them through which blood may pass as well (not shown) in the initial closed position. For this the leaflet (6) and the further leaflet (16) may be chamfered at the coaptating surface (12) and the further coaptating surface (112).

When the prosthetic valve is employed, tissue will grow on the scaffold (15) and on the further scaffold (115). The growth of tissue is a gradual process and the area of the scaffold (15) covered by the tissue will gradually increase. Blood cannot pass those areas of the scaffold (15) covered by tissue.

Similarly, the area of the further scaffold (115) covered by the tissue will gradually increase. Blood cannot pass those areas of the further scaffold (115) covered by tissue.

Figure 1D:
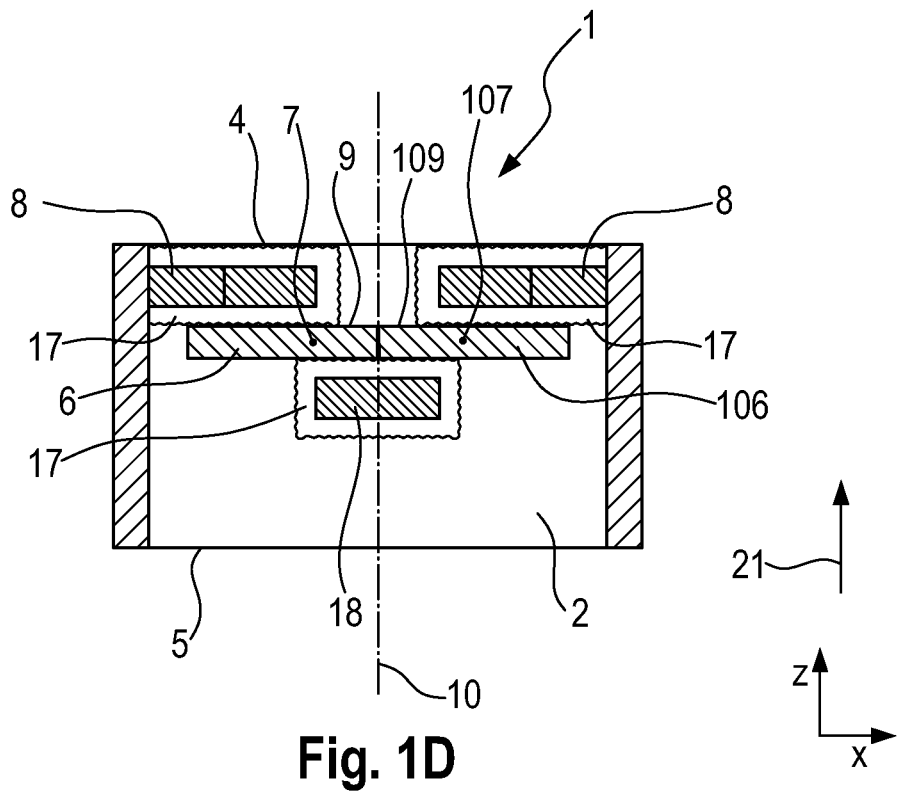

The closed status of the prosthetic valve (1) when the complete scaffold (15) and the complete further scaffold (115) is covered by tissue (17) is shown in FIG. 1D and will be referred to here as the final closed status which is obtained after a period of deployment of the prosthetic valve (1). This corresponds to a situation in which the regurgitation means have become ineffective.

In the final closed status the upstream surface (9) the tissue (17) on the scaffold (15) seals the one or more temporary openings in the scaffold (15). The upstream surface (9) and the further upstream surface (109) are perpendicular to the cylindrical axis (10) and the z-direction and the tissue (17) on the ridge (8) prevents further rotation of the leaflet (6) and the further leaflet (106). The coaptating surface (12) and the further coaptating surface (112) face each other and cooperatively prevent blood flow between them.

The prosthetic valve (1) also comprises a pair of additional ridges (18) arranged in the orifice (2) on the surrounding member (3). The additional ridges (18) are positioned downstream relative to the ridge (8) and the further ridge (108).

The additional ridges (18) are each formed by a scaffold. In the final closed status, the scaffold (15) and the further scaffold (115) are completely covered by tissue (17) which makes them larger. In the final closed status, the leaflet (6) and the further leaflet (106) are in contact with the tissue (17) on the additional ridges (18).

The additional ridges extend between a first x-coordinate and a second x-coordinate along an x-direction perpendicular to the z-direction and the y-direction, wherein the x-coordinate of the cylindrical axis (10) is in between the first x-coordinate and the second x-coordinate.

Figure 2A:
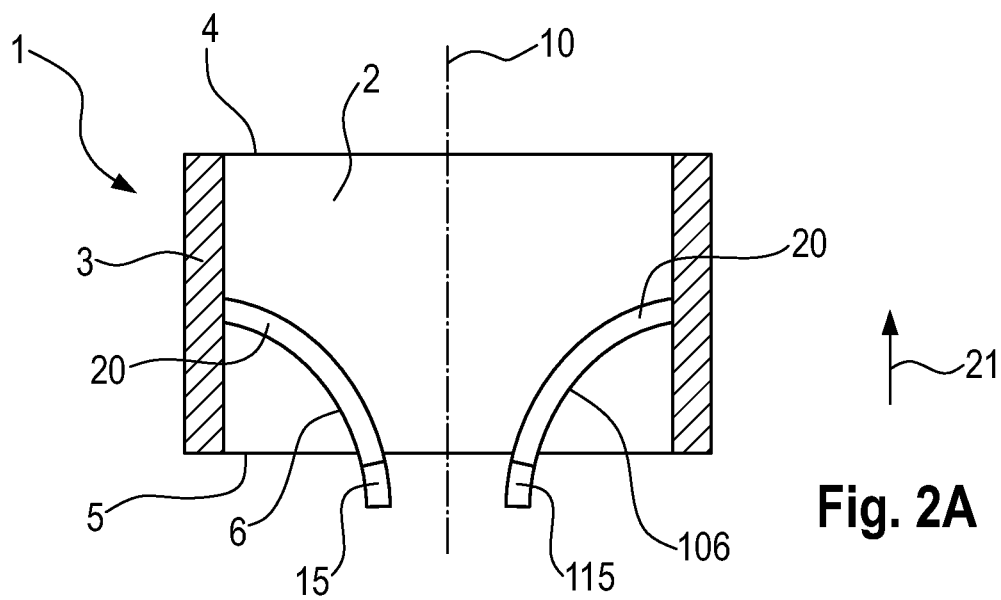
FIGS. 2A, 2B and 2C show cross sections of a prosthetic valve according to a second embodiment of the invention in respectively an open state, the initial closed state and the final closed state.

In a second embodiment of the invention, a prosthetic valve (1) comprises an orifice (2) arranged in a surrounding member (3). This embodiment is shown in FIGS. 2A, 2B and 2C.

The orifice (2) extends from an upstream side (4) to a downstream side (5). The orifice (2) is cylindrical and comprises a cylindrical axis (10) that intersects the upstream side (4) and the downstream side (5) and an orifice diameter. The prosthetic valve (1) is a mitral valve.

The prosthetic valve (1) comprises a leaflet (6) and a further leaflet (106) each comprising a leaflet member (20) made from a flexible organic material. Here both are leaflet members (20) are made from porcine tissue, more specifically from leaflets from a pig's heart. The leaflet member (20) of the leaflet (6) and the leaflet member (20) of the further leaflet (106) are attached to an inner surface (19) of the orifice (2) at opposite positions. The prosthetic valve (1) has an open valve status and a closed status. In the open status of the prosthetic valve (1), the leaflet (6) and the further leaflet (106) are in a corresponding open status. In the open status of the prosthetic valve (1) the leaflet (6) and the further leaflet (106) are bent away from each other, to maximally enable fluid flow between them. This status is shown in FIG. 2A. The leaflet (6) and the further leaflet (106) are moved and bent between their open status and their closed status in the same way as a natural leaflet in the mitral valve does.

Figure 2B:
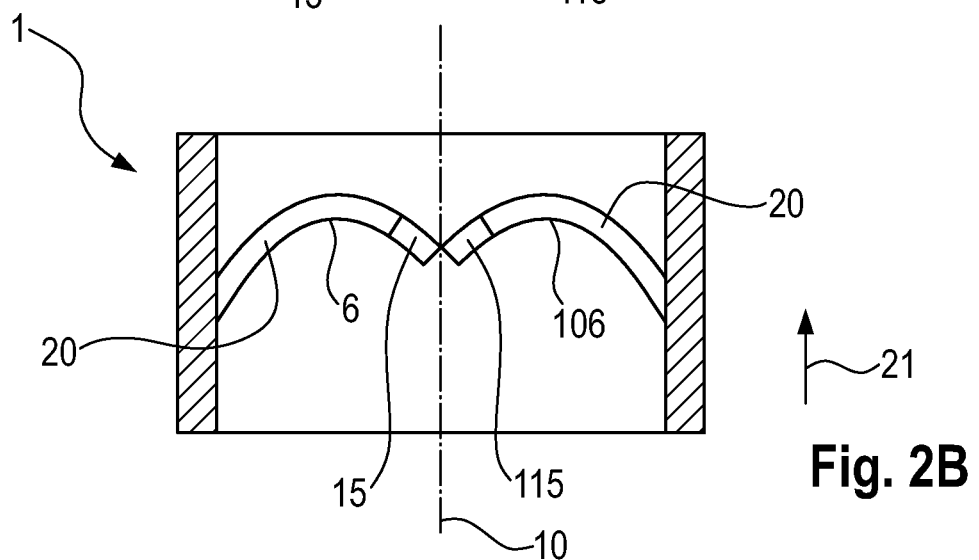
Figure 2C:
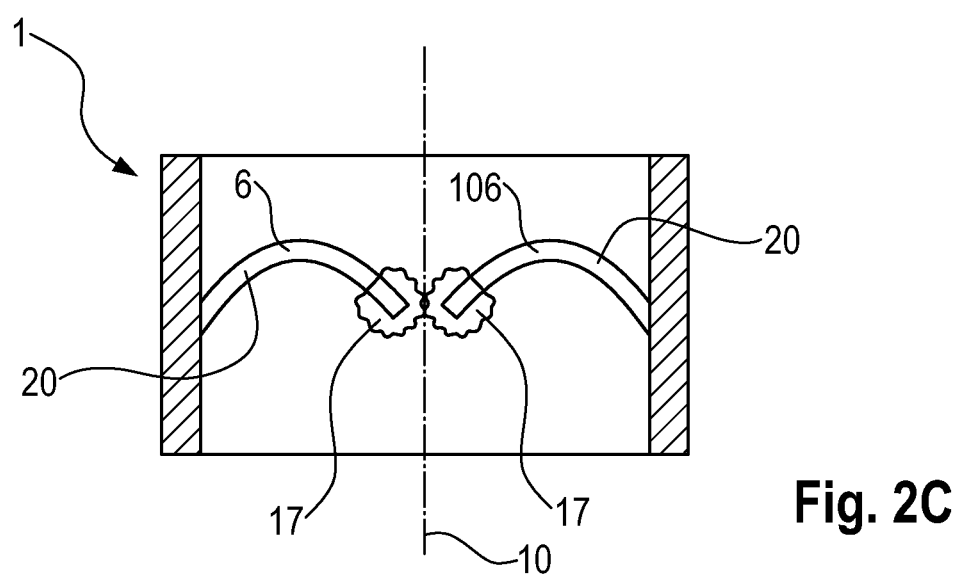

The closed status before deployment, here referred to as initial closed status, is depicted in FIG. 2B. In the closed status the leaflet (6) and the further leaflet (106) touch each other to restrict the blood flow through the orifice (2) in a restriction direction (21). Where the leaflet (6) and the further leaflet (106) are in contact with each other, the leaflet (6) and the further leaflet (106) comprise a scaffold (15) and a further scaffold (115) respectively. The scaffold (15) and the further scaffold (115) are attached to the leaflet members such that they form an extension of the leaflet members.

The scaffold (15) and the further scaffold (115) are made from a porous polylactide. The scaffold (15) and the further scaffold (115) are hemocompatible.

The scaffold (15) and the further scaffold (115) each comprise one or more temporary openings (11) formed by pores and allows blood to pass through the one or more temporary openings in a restriction direction (21) which runs from the downstream side (5) to the upstream side (4).

Thus, the scaffold (15) is a member that is comprised by regurgitation means. Similarly, the scaffold (115) is a member that is comprised by regurgitation means.

When the prosthetic valve is employed, tissue will grow on the scaffold (15) and on the further scaffold (115). The growth of tissue is a gradual process and the area of the scaffold (15) covered by the tissue will gradually increase. Blood cannot pass those areas of the scaffold (15) covered by tissue.

Similarly, the area of the further scaffold (115) covered by the tissue will gradually increase. Blood cannot pass those areas of the further scaffold (115) covered by tissue.

The closed status of the prosthetic valve (1) when the complete scaffold (15) and the complete further scaffold (115) is covered by tissue (17) is shown in FIG. 2C and will be referred to here as the final closed status, which is obtained after a period of deployment of the prosthetic valve (1). This corresponds to a situation in which the regurgitation means have become ineffective.

In the final closed status of the prosthetic valve (1), the tissue (17) on the leaflet (6) and the tissue (17) on the further leaflet (106) are in contact with each other and as blood cannot pass the scaffold (15) and the further scaffold (115), blood flow through the orifice (2) is completely restricted.

Figure 3:
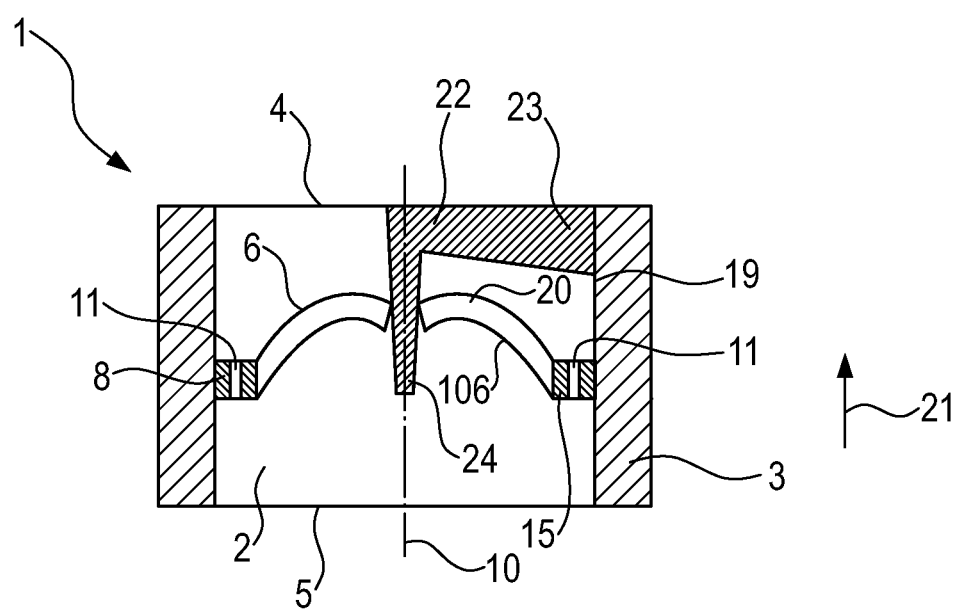
FIG. 3 shows a cross section of a prosthetic valve according to a third embodiment of the invention in an initial closed state.

In a third embodiment of the invention a prosthetic valve (1) comprises an orifice (2) arranged in a surrounding member (3). This embodiment is shown in FIG. 3.

The orifice (2) extends from an upstream side (4) to a downstream side (5). The orifice (2) is cylindrical and comprises a cylindrical axis (10) that intersects the upstream side (4) and the downstream side (5) and an orifice diameter. The prosthetic valve (1) is a mitral valve.

The prosthetic valve (1) comprises a leaflet (6) and a further leaflet (106) each comprising a leaflet member (20) made from a flexible organic material. Here both are leaflet members (20) are made from porcine tissue, more specifically from leaflets from a pig's heart.

At opposite positions, the leaflet member (20) of the leaflet (6) and the leaflet member (20) of the further leaflet (106) are attached to an annular ridge (8) that in turn is attached to an inner surface (19) of the orifice (2). The prosthetic valve (1) has an open valve status and a closed status. In the open status of the prosthetic valve (1), the leaflet (6) and the further leaflet (106) are in a corresponding open status. In the open status of the prosthetic valve (1) the leaflet (6) and the further leaflet (106) are bent away from each other, to maximally enable fluid flow between them.

The annular ridge (8) is formed by a scaffold (15). The scaffold (15) is made from a porous polylactide. The scaffold (15) is hemocompatible.

The scaffold (15) has pores that form temporary openings (11) that allow regurgitation in a restriction direction (21) which runs from the downstream side (5) to the upstream side (4). As tissue grows onto the scaffold (15) the temporary openings (11) gradually are closed and regurgitation is diminished.

The leaflet (6) and the further leaflet (106) are moved and bent between their open status and their closed status in the same way as a natural leaflet in the mitral valve does.

The prosthetic valve (1) also comprises a strut (22) made from biodegradable material, here from a mixture of polyanhydrides. The strut (22) is attached to the inner surface (19) of the on a position upstream of the annular ridge (8). The strut (22) is attached to the inner surface (19) at a first end (23). The strut comprises two ends and is tapered from the first end (23) to the other end, the second end (24). The second end (24) points in the direction from the upstream side (4) to the downstream side (5) and is positioned on the cylindrical axis (10).

The edge of the leaflet (6) and the further leaflet (106) have a constant lengths. The lengths of the edges of the leaflet (6) and the further leaflet (106) are arranged to provide contact between the leaflet (6) and the further leaflet (106) and close the orifice (2) in the closed state without a strut (22) (not shown). However, when the prosthetic valve is freshly employed, the second end (24) is in between the leaflet (6) and the further leaflet (106). Therefore leaflet (6) and the further leaflet (106) cannot reach the status that they would reach if the strut (22) would not have been present. To prevent regurgitation at the strut (22), the edge of the leaflet (6) and the further leaflet (106) would be following the strut (22) where the strut is in between the leaflet (6) and the further leaflet (106) which would require a larger length of the edge of the leaflet (6) and the further leaflet (106). Therefore, in the area next to the strut (22) the leaflet (6) and the further leaflet (106) will not completely close the orifice (2) and regurgitation in a restriction direction (21) which runs from the downstream side (5) to the upstream side (4) will be possible.

In use, the strut (22) will become thinner and thinner as it is made from biodegradable material. As the strut (22) is tapered from the first end (24), where it is attached to the surrounding member (3) to the second end (25), the strut will maintain its integrity and will not break but will slowly disappear from the second end (25) to the first end (24).

After a period of deployment of the prosthetic valve (1) the strut (22) will have degraded completely, i.e. will no longer be present in the prosthetic valve (1).

In this embodiment the scaffold (15) and the strut (22) are each regurgitation means that can be used independently or as explained in combination.

Figure 4A:
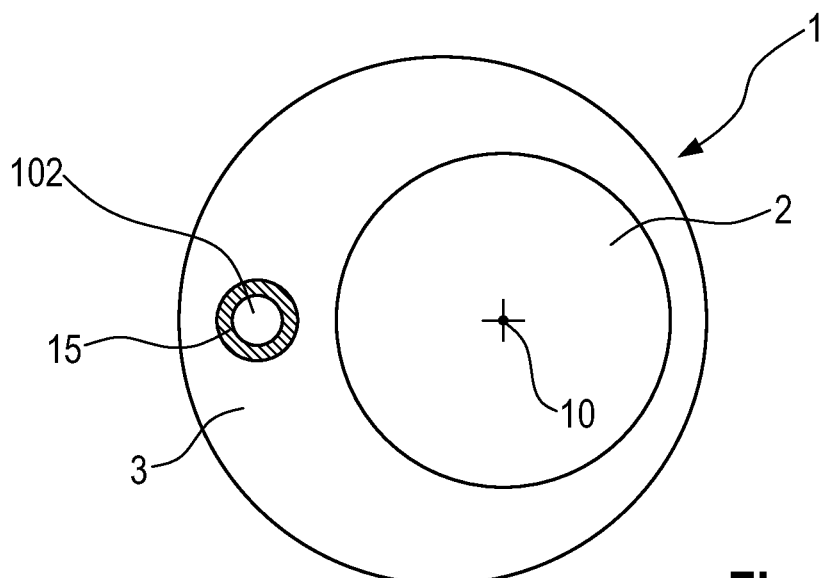
FIG. 4A and FIG. 4B show a downstream view and a cross section of a prosthetic valve according to a fourth embodiment of the invention.
Figure 4B:
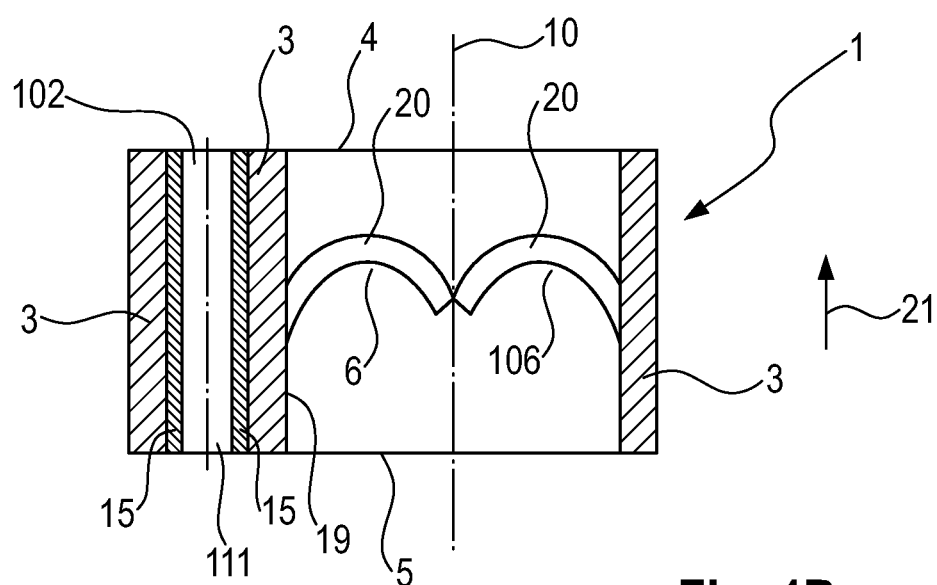

In a fourth embodiment of the invention a prosthetic valve (1) comprises an orifice (2) arranged in a surrounding member (3). This embodiment is shown in FIG. 4A and FIG. 4B in a closed state of the prosthetic valve (1). For clarity the leaflet (6) and the further leaflet (106) are not shown in FIG. 4A.

The orifice (2) extends from an upstream side (4) to a downstream side (5). The orifice (2) is cylindrical and comprises a cylindrical axis (10) that intersects the upstream side (4) and the downstream side (5) and an orifice diameter. The prosthetic valve (1) is a mitral valve.

The prosthetic valve (1) comprises a leaflet (6) and a further leaflet (106) each comprising a leaflet member (20) made from a flexible organic material. Here both are leaflet members (20) are made from porcine tissue, more specifically from leaflets from a pig's heart.

The leaflet member (20) of the leaflet (6) and the leaflet member (20) of the further leaflet (106) are attached to an inner surface (19) of the orifice (2) at opposite positions. The prosthetic valve (1) has an open valve status and a closed status. In the open status of the prosthetic valve (1), the leaflet (6) and the further leaflet (106) are in a corresponding open status. In the open status of the prosthetic valve (1) the leaflet (6) and the further leaflet (106) are bent away from each other, to maximally enable fluid flow between them. The leaflet (6) and the further leaflet (106) are moved and bent between their open status and their closed status in the same way as a natural leaflet in the mitral valve does.

Before employing the prosthetic valve (1), the surrounding member (3) comprises a further orifice (102) that extends from the upstream side (4) to the downstream side (5). The further orifice (102) is at partially filled with a scaffold (15). The scaffold is biodegradable. The scaffold is made from a porous polylactide. The scaffold is hemocompatible.

The scaffold is a relatively open structure and comprises pores. The pores form temporary openings (11) through which blood can flow in a restriction direction (21) which runs from the downstream side (5) to the upstream side (4). As the further orifice (102) is only partly filled with the scaffold (15) it comprises an additional temporary opening (111) through which blood can flow.

After a period of deployment, a tissue completely covers the scaffold and completely fills the temporary openings (11) and the additional temporary opening (111). Blood cannot flow through the tissue. Therefore, after the period of deployment, the regurgitation means (102, 15) have become ineffective.

In a variant of the embodiment, the further orifice (102) is completely filled with the scaffold even before use.

Figure 5A:
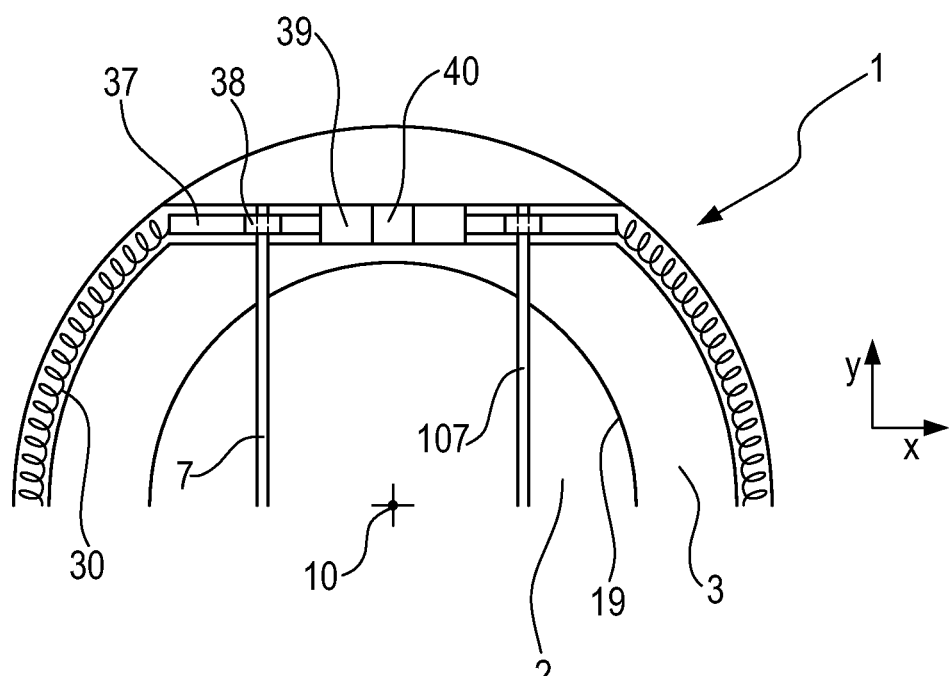
FIG. 5A and FIG. 5B show different views of a prosthetic valve according to a fifth embodiment of the invention.
Figure 5B:
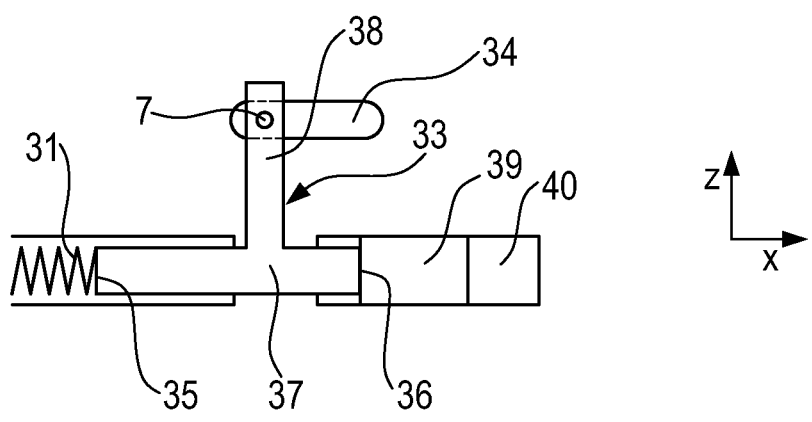

In a fifth embodiment of the invention, a prosthetic valve (1) comprises an orifice (2) arranged in a surrounding member (3). This embodiment is depicted in FIG. 5A and FIG. 5B. The orifice (2) extends from an upstream side (4) to a downstream side (5). The orifice (2) is cylindrical and comprises a cylindrical axis (10) that intersects the upstream side (4) and the downstream side (5) and an orifice diameter. The orifice (2) is surrounded by an inner surface (19). The prosthetic valve (1) is a mitral valve.

The cylindrical axis (10) runs in a z-direction of an orthogonal, Cartesian coordinate system.

The prosthetic valve (1) comprises a leaflet (6). The leaflet is suspended in the orifice (2) by an axle (7) around which it can rotate. The prosthetic valve (1) comprises a further leaflet (106) that is suspended in the orifice (2) by a further axle (107) around which it can rotate.

The axle (7) and the further axle (107) run in a y-direction, perpendicular to the z-direction.

The leaflet (6) and the further leaflet (106) are displaceable by being rotable by the blood flow. The leaflet (6) comprises an upstream surface (9) and the further leaflet (106) comprises a further upstream surface (109). The upstream surface (9) of the leaflet (6) and the further upstream surface (109) of the further leaflet (106) each form half a circle, complementing each other to form a full circle.

The diameter of the half circle formed by both the leaflet (6) and the further leaflet (106) is almost as large as the orifice diameter. The leaflet (6) comprises a coaptating surface (12) and the further leaflet (106) comprises a further coaptating surface (112).

The prosthetic valve (1) has an open status and a closed status. In the open status the leaflet (6) and the further leaflet (106) are in an open position and a further open position respectively.

In the open status, the upstream surface (9) and the further upstream surface (109) face away from each other.

In the open position the cylindrical axis (10) is parallel to the upstream surface (9). In the open position, the coaptating surface (12) and the further coaptating surface (112) face toward the upstream side (4).

In the closed status the leaflet (6) and the further leaflet (106) cooperate to close the orifice (2).

The surrounding member (3) comprises a spring-loaded mechanism embedded in the surrounding member (3). Before employment of the prosthetic valve (1), the spring-loaded mechanism is winded. The spring-loaded mechanism comprises a first mechanism.

The first mechanism comprises a spring (30). The spring extends in a tubular space in the surrounding member (3). The tubular space comprises a central axis. The central axis lies in a plane perpendicular to the z-axis.

The spring comprises a first end (31) and a second end (not shown). The first end exerts a pushing force against a first surface (35) of an axle support (33) in an x-direction. The x-direction is perpendicular to the z-direction and the y-direction. The axle support (33) comprises a foot (37) and a pillar (38), the pillar (38) comprising a through hole. The axle (7) sticks trough the through hole. The axle (7) also sticks through a slit (34) arranged in the surrounding member (3). The axle support (33) comprises a second surface (36). The second surface (36) and the first surface (35) are on opposite sides of the axle support (33) and face away from each other. The second surface (36) is pushed by the spring (30) against a timing member (39) made of biodegradable material.

In turn, the timing member forwards a part of the force exerted by the spring to a stopping member (40). The stopping member (40) and the slit (34) have fixed relative positions.

A first end (371) of the foot (37) is slidably placed in the tubular space. A second end (372) of the foot (37) is positioned in another tubular space which ends at the timing member (39).

When the prosthetic valve (1) is in use and the biodegradable material degrades, the volume of the timing member (39) decreases. This makes that the spring will unwind and will push the axle support (33) towards the stopping member. As the axle (7) is supported by the axle support (33), the axle (7) is also pushed towards the stopping member (40).

At the other end of the spring, the construction is repeated to support the other end of the axle (7). The first mechanism is mirrored to form a second mechanism comprised in the spring-loaded mechanism and for instance comprises a further spring (130). The second mechanism supports the further axle (107) on both ends.

As the axle (7) is pushed towards the stopping member (40), the distance between the axle (7) and the further axle (107) decreases. Similarly, the distance between the axle (7) and the further axle (107) decreases when the further axle (107) is pushed towards the stopping member (40).

In use, regurgitation is achieved in the prosthetic valve (1) initially because the axle (7) and the further axle (107) are at a too large distance for the leaflet (6) and the further leaflet (106) to fully cover the orifice (2). As the axle (7) and the further axle (107) are pushed towards each other, the leaflet (6) and the further leaflet (106) get to a position wherein they do fully cover the orifice (2) in a closed state. This position corresponds to the position wherein the second surface (36) of the axle support (33) is in contact with the stopping member (40) with the similar situation at the other end of the spring and at the second mechanism.

In a variant of the fifth embodiment, the timing member (39) comprises a series of regions with different degradation characteristics. The degradation characteristics in a first variant differ because the biodegradable material itself in a first timing region (39) that the axle support (33) encounters degrades faster than the biodegradable material in the second region that the axle support (33) encounters.

In a second variant the degradation characteristics differ although the biodegradable material in the first region is the same as that in the second region. However, the second region is larger, such that it takes longer to fully degrade.

In another variant of the fifth embodiment, the timing member (39) is not placed against the stopping member (40) but the space between the timing member (39) and the stopping member (40) is left empty. The effect is that if the timing member (39) has degraded, the axle support (33) slides suddenly trough the empty space as the spring (30) unwinds.

The above embodiments should be regarded as illustrative rather than restrictive, and it should be appreciated that variations may be made in those embodiments by a person skilled in the art without departing from the scope of the present invention as defined in the following claims. For instance, in the first and the second embodiment, the scaffold may be not be degradable. Where the scaffold is degradable it is preferably degradable at a rate slower than the rate of formation of tissue on the scaffold. Therefore, preferably, the scaffold (15) of the first embodiment may be made from degradable polyester such as poly lactides or poly glycolides.

Advantageous materials for the strut degrade within a timeframe of a few weeks. In addition, the advantageous material show surface degradation instead of bulk degradation, are bioresorbable, biocompatible, resemble soft tissue properties, show nonlinear stress-streain behavior, a Young's modules compatible with soft tissues and show stability under cyclic loading. Polyanhydrides and PGS (polyglycerol sebacate) are examples such advantageous materials. Thus alternately the strut may be made from a single polyanhydride, a mixtures of polyanhydrides or PGS.

Also, in a variant of the fifth embodiment, the spring of the spring loaded mechanism may be unwinded by the rhythmic opening of the valves. In that case the energy corresponding to the hemodynamically induced movement of the leaflet is used to unwind the spring. In an embodiment using a spring-loaded mechanism, the spring may unwind itself at the desired rate.

In yet other variants of the invention the prosthetic valve (1) is an aortic or a tricuspid valve. In further variants the prosthetic valve (1) comprises a different number of leaflets, such a one or three.

The invention claimed is:

1. A prosthetic valve for regulating fluid flow between an upstream side and a downstream side and being operable between an open status and a closed status, comprising:
    an orifice arranged in a surrounding member and extending between the upstream side and the downstream side, wherein in the open status of the prosthetic valve the fluid flow through the orifice is maximally enabled, and wherein in the closed status of the prosthetic valve the fluid flow through the orifice in a restriction direction from the downstream side to the upstream side is restricted;
    a first leaflet arranged in the orifice and being operable between an open status corresponding to the open status of the prosthetic valve and a closed status corresponding to the closed status of the prosthetic valve; and
    a regurgitation element arranged in the prosthetic valve for achieving regurgitation in the restriction direction and arranged for becoming ineffective after a period of deployment, the regurgitation element including a member arranged in the orifice in the surrounding member or the first leaflet, the member further arranged to leave a temporary opening in the orifice in the closed status of the prosthetic valve,
    wherein the member promotes tissue growth on the member itself, the tissue growth gradually extending tissue over the temporary opening until the temporary opening is covered.

2. The prosthetic valve according to claim 1, wherein the member is a scaffold.

3. The prosthetic valve according to claim 1, further comprising a second leaflet arranged in the orifice and being operable between an open status corresponding to the open status of the prosthetic valve and a closed status corresponding to the closed status of the prosthetic valve, wherein the member is attached to the first leaflet leaving the temporary opening between the first leaflet and the second leaflet.

4. A prosthetic valve for regulating fluid flow between an upstream side and a downstream side and being operable between an open status and a closed status, comprising:
    an orifice arranged in a surrounding member and extending between the upstream side and the downstream side wherein in the open status of the prosthetic valve the fluid flow through the orifice is maximally enabled and wherein in the closed status of the prosthetic valve the fluid flow through the orifice in a restriction direction from the downstream side to the upstream side is restricted;
    a first leaflet arranged in the orifice and being operable between an open status corresponding to the open status of the prosthetic valve and a closed status corresponding to the closed status of the prosthetic valve; and
    a regurgitation element arranged in the prosthetic valve for achieving regurgitation in the restriction direction and arranged for gradually becoming ineffective after a period of deployment, the regurgitation element including a member arranged in the orifice in the surrounding member or the first leaflet, the member further arranged to leave a temporary opening in the orifice in the closed status of the prosthetic valve,
    wherein the member promotes tissue growth on the member itself, the tissue growth gradually extending tissue over the temporary opening until the temporary opening is covered.

5. The prosthetic valve according to claim 4, wherein the member is attached to the surrounding member or the first leaflet, such that the prosthetic valve comprises the temporary opening between the surrounding member and the first leaflet.

6. The prosthetic valve according to claim 4, comprising a second leaflet arranged in the orifice and being operable between an open status corresponding to the open status of the prosthetic valve and a closed status corresponding to the closed status of the prosthetic valve, wherein the member is attached to the first leaflet leaving the temporary opening between the first leaflet and the second leaflet.

7. The prosthetic valve according to claim 4, wherein the member is a scaffold.

* * * * *